(12) United States Patent
Brieva et al.

(10) Patent No.: US 8,557,263 B1
(45) Date of Patent: Oct. 15, 2013

(54) COSMETIC COMPOSITION IN THE FORM OF AN OIL-IN-WATER EMULSION

(75) Inventors: Patricia Brieva, Manalapan, NJ (US); Angelike Galdi, Westfield, NJ (US); Jean-Thierry Simonnet, Mamaroneck, NY (US); Anthony Potin, Hoboken, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/434,531

(22) Filed: Mar. 29, 2012

(51) Int. Cl.
 *A61K 8/02* (2006.01)
(52) U.S. Cl.
 USPC .......................................................... 424/401
(58) Field of Classification Search
 None
 See application file for complete search history.

(56) References Cited

U.S. PATENT DOCUMENTS

| | | | |
|---|---|---|---|
| 6,039,935 A * | 3/2000 | Mohammadi | 424/59 |
| 2002/0044913 A1* | 4/2002 | Hamilton | 424/59 |
| 2005/0196347 A1* | 9/2005 | Berillouet et al. | 424/47 |

FOREIGN PATENT DOCUMENTS

| | | |
|---|---|---|
| WO | 9732560 | 12/1997 |
| WO | 0040214 | 7/2000 |

* cited by examiner

*Primary Examiner* — Carlos Azpuru
*Assistant Examiner* — Casey Hagopian
(74) *Attorney, Agent, or Firm* — McNees, Wallace & Nurick, LLC

(57) ABSTRACT

A cosmetic composition in the form of an oil-in-water emulsion methods of using and producing cosmetic compositions is provided. The cosmetic composition includes an aqueous phase, an oil phase comprising a water-in-oil emulsifier, and an oil stabilizing component. The water-in-oil emulsifier is at concentration, by weight, of about 0.01% to about 6.0%, based upon weight of the composition. The oil stabilizing component includes one or both of an amphiphilic compound or a surfactant having an HLB of 13 or greater added to the aqueous phase. The oil stabilizing component is at a concentration, by weight, of about 0.01% to about 1.0%, based upon weight of the composition. The oil-in-water emulsion has an increased water load relative to water-in-oil emulsions without having an increased viscosity.

17 Claims, No Drawings

COSMETIC COMPOSITION IN THE FORM OF AN OIL-IN-WATER EMULSION

FIELD OF THE INVENTION

The present invention is directed to cosmetic compositions and methods of using and producing cosmetic compositions. More specifically, the present invention is directed to a cosmetic composition having oil-in-water emulsions and methods of using and producing cosmetic compositions including a water-in-oil emulsifier having a concentration, by weight, of about 0.01% to about 6.0%, and an oil stabilizing component having a concentration, by weight, of about 0.01% to about 1.0%, based upon the weight of the composition.

BACKGROUND OF THE INVENTION

For various reasons associated in particular with greater comfort of use (softness, emollience and the like), current cosmetic compositions are usually in the form of an emulsion of the oil-in-water (O/W) type consisting of an aqueous-dispersing-continuous phase and an oily-dispersed-discontinuous phase, or of an emulsion of the water-in-oil (W/O) type consisting of an oily-dispersing-continuous phase and an aqueous-dispersed-discontinuous phase. O/W emulsions are the ones most sought in the cosmetics field, since O/W emulsions comprise an aqueous phase as external phase, which gives them, when applied to the skin, a fresher, less greasy and lighter feel than W/O emulsions.

Standard O/W emulsions are generally stabilized with amphiphilic molecules such as emulsifying surfactants of the alkylglycerol or alkylpolyoxyethylene type. However, these surfactants have the drawback of inducing a waxy, heavy feel.

W/O emulsions are often stabilized with silicone elastomeric polymers. Silicone elastomeric polymers may have a nice cosmetic feel but W/O emulsions containing silicone elastomeric polymers are limited in terms of formula robustness and aesthetics.

Therefore, it is desirable to provide a cosmetic composition and methods of using and producing cosmetic compositions in the form of oil-in-water emulsions that do not suffer from one or more of the above drawbacks and oil-in-water emulsions that have a nice cosmetic feel.

BRIEF DESCRIPTION OF THE INVENTION

In an exemplary embodiment, a cosmetic composition is in the form of an oil-in-water emulsion. The cosmetic composition includes an aqueous phase, an oil phase including a water-in-oil emulsifier, and oil stabilizing component. The water-in-oil emulsifier is at a concentration, by weight, of about 0.01% to about 6.0%, based upon weight of the composition. The oil stabilizing component includes one or both of an amphiphilic compound, a surfactant having an HLB of 13 or greater, or a combination thereof added to the aqueous phase. The oil stabilizing component is at a concentration, by weight, of about 0.01% to about 1.0%, based upon weight of the composition. The oil-in-water emulsion of the present invention has an increased water load relative to water-in-oil emulsions without having an increased viscosity.

Other features and advantages of the present invention will be apparent from the following more detailed description of the preferred embodiment which illustrates, by way of example, the principles of the invention.

DETAILED DESCRIPTION OF THE INVENTION

"Keratinous tissue," as used herein, includes but is not limited to skin, hair, and nails.

"Homogenous" means substantially uniform throughout, i.e., a single phase mixture.

In the present application the term "ambient temperature" means a temperature of 25° C.

The cosmetic compositions and methods of the present invention can comprise, consist of, or consist essentially of the essential elements and limitations of the invention described herein, as well as any additional or optional ingredients, components, or limitations described herein or otherwise useful in personal care compositions intended for topical application to keratinous tissue.

It has been surprisingly discovered by the inventors that a water-in-oil emulsifier and a predetermined concentration of an oil stabilizing component including one or both of an amphiphilic compound, a surfactant having an HLB greater than 13 added to the aqueous phase or oil phase yields an oil-in-water emulsion having an increased water load relative to water-in-oil emulsions without having an increased viscosity.

The cosmetic composition in the form of an oil-in-water emulsion includes an aqueous phase, an oil phase including a water-in-oil emulsifier, and an oil stabilizing component. The oil stabilizing component includes one of both of an amphiphilic compound or a surfactant having an HLB of 13 or greater. The oil stabilizing component is at a concentration, by weight, of about 0.01% to about 1.0%, or alternatively about 0.05% to about 0.8%, or alternatively about 0.09% to about 0.5%, or alternatively about 0.1%, based upon the weight of the composition. The cosmetic composition in the form of an oil-in-water emulsion having an increased water load relative to water-in-oil emulsions without having an increased viscosity.

Aqueous Phase

The aqueous phase present in the cosmetic composition according to the disclosure includes water, a preservative, glycerin, and a chelating agent. In one embodiment, the aqueous phase comprises, by weight, about 60% to about 85%, or alternatively 65% to about 83%, or alternatively about 70% to about 82%, based upon weight of the composition. The preservative is at a concentrations, by weight, about 0.1% to about 0.7%, or alternatively, about 0.2% to about 0.6%, or alternatively about 3.5% to about 5%, based upon weight of the composition. Suitable examples of preservatives include, but are not limited to, phenoxyethanol, ethylhexylglycerin, chlorphenesin. In one embodiment, the chelating agent is at a concentration, by weight, of about 0.05% to about 0.25%, or alternatively about 0.06% to about 0.20%, or alternatively about 0.8% to about 0.15%, based upon weight of the composition. Suitable examples of chelating agents include, but are not limited to, disodium EDTA, tetrasodium EDTA, and combinations thereof.

The aqueous phase may also contain cosmetically acceptable additives or adjuvants as well as cosmetic or dermatologic active agents. Representative additives and adjuvants include, for example, water-soluble or water-miscible solvents or co-solvents, humectants, moisturizers, colorants, fillers, preservatives, antioxidants (e.g., EDTA, BHT, tocopherol), essential oils, fragrances, dyes, neutralizing or pH-adjusting agents (e.g., triethylamine (TEA) and sodium hydroxide), conditioning or softening agents (e.g., panthenol, allantoin and glycerin) and extracts such as botanical extracts. Additives and adjuvants may be present in the compositions in amounts generally ranging from about 0.01% to about 10% by weight. Examples of cosmetic active agents or dermatological active agents include sunscreen agents, free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents.

Oil Phase

The oil phase present in the composition according to the disclosure includes PEG-10 dimethicone, dimethicone, an emollient, propylene carbonate, and an active ingredient. Examples of suitable emollients, includes but are not limited to, hydrogenated polyisobutene and isohexadecane.

In one embodiment, the active ingredient is capryloyl salicylic acid.

Water-in-Oil Emulsifier

The water-in-oil emulsifier present in the cosmetic composition according to the disclosure includes a polyether modified silicon crosspolymers, such as, dimethicone and dimethicone/PEG-10/15 Crosspolymer, under the tradename KSG-210, available from Shin-Etsu Silicones of America, Inc., Akron, Ohio.

The water-in-oil emulsifier is advantageously present at a concentration, by weight, of about 1.0% to about 6.0%, or alternatively about 1.5% to about 5.0%, or alternatively about 2.0% to about 4.0%, based upon weight of the composition.

Amphiphilic Compound

Amphiphilic compounds are compounds comprising one or more hydrophilic parts that make them partially water-soluble and one or more hydrophobic parts via which associate or interact with an oily phase. The amphiphilic compound present in the cosmetic composition according to the disclosure includes C8-C10 glycol, caprylyl glycol, combinations thereof.

The amphiphilic compound is advantageously present at a concentration, by weight, of about 0.01% to about 5.0%, or alternatively about 0.05% to about 2.0%, or alternatively about 0.08% to about 0.5%, based upon weight of the composition.

Surfactant

The surfactant is present in the cosmetic composition alone or in combination with the amphiphilic compound according to the disclosure has a HLB of 13 or greater. In one embodiment, the HLB is between 13 and 18, or alternatively between 14 and 17, or alternatively between 15 and 16.

Suitable examples of compounds having a HLB of 13 or greater are polysorbates. Examples of suitable polysorbates are Polysorbate 20, which has a HLB of about 16.7, Polysorbate 60, which has a HLB of about 14.9, Polysorbate 60 NF, which has a HLB of about 14.9, Polysorbate 80, which has a HLB of about 15, and Polysorbate 80 NF which has a HLB of about 15.

Other suitable examples of compounds having a HLB of 13 or greater are alkyl esters, ether oxyethylene (Brij and Myrj series), sucrose alkyl esters, and combinations thereof.

The surfactant is advantageously present at a concentration, by weight, of about 0.01% to about 2.0%, or alternatively about 0.05% to about 0.8%, or alternatively about 0.08% to about 0.5%, based upon weight of the composition.

Thickening Phase

The cosmetic composition of the present disclosure optionally includes a thickening phase. The thickening phase comprises dimethicone, sodium polyacrylate, and combinations thereof.

Mattifier

The cosmetic composition of the present invention optionally includes at least one mattifier. The mattifier includes acrylate copolymer, Nylon-12, polyamides, and combinations thereof.

The cosmetic composition of the present invention has a viscosity measured at a temperature of about 20° C. to about 25° C. of 40 Pascal second (Pa·s) to about 120 Pa·s, or alternatively about 60 Pa·s to about 100 Pa·s, or alternatively about 65 Pa·s to about 85 Pa·s. The viscosity was measured with a Viscometer Rheomat at 25° C. The water-in-oil (W/0) emulsions were measured with Spindle No. 3 at 200 rpm rotations per min at 25° C. for 10 minutes. The oil-in-water (O/W) emulsions were measured with Spindle No. 3 at 200 rpm rotations per min at 25° C.

The method for treating keratinous tissue includes applying to the keratinous tissue the cosmetic composition of the present disclosure. The oil-in-water emulsion obtained using the composition of the present disclosure are suitable for applications to the skin, such as such as, but not limited to, skincare lotions and skin care creams.

The process of preparing the oil-in-water emulsion of the present disclosure includes homogenizing at a predetermined temperature the oil phase comprising the water-in-oil emulsifier. The oil phase includes PEG-10 dimethicone, dimethicone, an emollient, propylene carbonate, and an active ingredient. The predetermined temperature is approximately 40° C. to about 70° C. and homogenization occurs using a mixer. The process includes adding the oil stabilizing component to the homogenized oil phase. The process includes mixing the aqueous phase with the oil phase to form the oil-in-water emulsion.

EXAMPLES

TABLE 1

| | | Examples | | | | |
|---|---|---|---|---|---|---|
| Phase | INCI Name | 1 | 2 | 3 | 4 | 5 |
| A | Disteardimonium Hectorite | 0.6 | 0.6 | 0.6 | 0.6 | 0.6 |
| A | Titanium Dioxide and Mica | 0.1 | 0.1 | 0.1 | 0.1 | 0.1 |
| A | Capryloyl Salicylic Acid | 0.1 | 0.1 | 0.1 | 0.1 | 0.1 |
| A | Dimethicone and Dimethicone/PEG-10/15 Crosspolymer (KSG-210) | 3.6 | 3.6 | 3.6 | 3.6 | 3.6 |
| A | Hydrogenated Polyisobutene | 6 | 6 | 6 | 6 | 3 |
| A | PEG-10 Dimethicone | 0.5 | 0.5 | 0.5 | 0.5 | 0.5 |
| A | Propylene Carbonate | 0.2 | 0.2 | 0.2 | 0.2 | 0.2 |
| B | Phenoxyethanol | 0.5 | 0.5 | 0.5 | 0.5 | 0.5 |
| B | Water | 69.7 | 69.6 | 69.5 | 69.3 | 75.2 |
| B | Disodium EDTA | 0.15 | 0.15 | 0.15 | 0.15 | 0.15 |
| B | Glycerin | 10 | 10 | 10 | 10 | 10 |
| B | Caprylyl Glycol | — | 0.1 | 0.1 | 0.4 | — |
| B | Polysorbate 20 | — | — | 0.1 | — | — |
| C | Dimethicone | 6 | 6 | 6 | 6 | 3.5 |
| C | Sodium Polyacrylate | 1.5 | 1.5 | 1.5 | 1.5 | 1.5 |
| D | Nylon-12 | 1 | 1 | 1 | 1 | 1 |
| D | Acrylates Copolymer | 0.05 | 0.05 | 0.05 | 0.05 | 0.05 |
| | Total (wt/wt %) | 100 | 100 | 100 | 100 | 100 |
| | Viscosity (Pa · s)*** | 76.8 | 59.3 | 77 | 61.6 | 112 |
| | Type of Emulsion | W/O | O/W | O/W | O/W | O/W |
| | Conductivity | no | yes | yes | yes | yes |

***Viscometer Rheomat: W/O measured with Spindle No. 3 at 200 rpm rotations per min at 25° C. for 10 minutes. O/W measured with Spindle No. 3 at 200 rpm rotations per min at 25° C.

Procedure

Added phase A (oil phase) to the main kettle and heated to about 55° C. to about 62° C. and mixed and homogenized to disperse all compounds in the oil phase. In a separate beaker, heated phase B (aqueous phase) to 55° C. to about 62° C. Combined phase A and phase B while homogenizing at 55° C. to about 62° C. After about 10 minutes the temperature was dropped to room temperature (about 20° C. to about 25° C.).

The mixture was held at room temperature for about 10 minutes, then temperature of the mixture was raised to about 35° C. to about 45° C. and the phase C was added. Phase D was added while the mixture was still at about 35° C. to about 45° C. Heat was removed and mixture was mixed until the temperature is less than 30° C.

Example 1 is a standard water-in-oil emulsion prepared using the water-in-oil emulsifier. Examples 2-4 are oil-in-water emulsions prepared according to an embodiment of the present disclosure.

An emulsion verification tool was used to determine the type of emulsion. The emulsion type was established using Fisher Scientific Traceable Multimeter that measures conductivity. For oil-in water emulsions the external phase is water and water conducts electricity, thus a reading was measured in Ohms. For water-in-oil emulsions, the external phase is oil and oil does not conduct so no conductivity was measured for water-in-oil emulsions, which was represneted as zero, not available or O.L. on the multimeter. As shown in Table 1, above, Example 1 is a water-in-oil (W/O) emulsion and Examples 2-4 are oil-in-water (O/W) emulsions. The addition of the small amount of an amphiphilic compound such as C8-C10 glycol, or a surfactant, such as Polysorbate 20, having an HLB of 13 or greater at an amount as low as 0.1% as shown by Examples 2-4 surprisingly results oil-in-water emulsions even though using water-in-oil emulsification system, namely Dimethicone and Dimethicone/PEG-10/15 Crosspolymer (KSG-210) available from Shin-Etsu Silicones of America, Inc., Akron, Ohio. The resulting oil-in-water emulsions have a viscosity substantially that of water-in-oil emulsions, such as the one provided in Example 1. Additionally, the oil-in-water emulsions of Examples 2-4 increase water content while maintaining the oil-in-water emulsion structure or cosmeticity of the formulation.

The oil-in-water composition of the present disclosure allows for higher water content, while allowing the formulation to maintain its external phase (water phase). In contrast, if the system were a W/O emulsion, where the water is in the internal phase and oil is the external phase, then droplet size of the internal water phase would increase as water is added and may eventually may break thereby inverting the emulsion to an oil-in-water emulsion. In Example 5, the water-in-oil emulsion of Example 1 was modified by increasing water content by 5% and decreasing oil content by 5%, which resulted in an emulsion that could no longer maintain its architecture and converted to an Oil-in-Water emulsion. Additionally, the viscosity of the oil-in-water emulsion of Example 5 has an increased viscosity of 112 Pa·s. Thus, the Oil-in-Water emulsion of the present disclosure is much more stable and is able to maintain the emulsion type if additional water needs to be added to the composition or formulation.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cosmetic composition in the form of an oil-in-water emulsion comprising:
   an aqueous phase;
   an oil phase comprising a water-in-oil emulsifier, wherein the water-in-oil emulsifier comprises a polyether modified silicone crosspolymer and the water-in-oil emulsifier is at a concentration, by weight, of about 0.01% to about 6%, based upon weight of the composition, wherein the oil phase further comprises PEG-10 dimethicone, dimethicone, an emollient, propylene carbonate, and an active ingredient; and
   an oil stabilizing component including one or both of an amphiphilic compound or a surfactant having an HLB of 13 or greater added to the aqueous phase, wherein the oil stabilizing component is at a concentration, by weight, of about 0.01% to about 1.0%, based upon weight of the composition;
   wherein the oil-in-water emulsion has an increased water load relative to water-in-oil emulsions without having an increased viscosity.

2. The cosmetic composition of claim 1, wherein the amphiphilic compound comprises C8-C10 glycol.

3. The cosmetic composition of claim 1, wherein the amphiphilic compound comprises caprylyl glycol.

4. The cosmetic composition of claim 1, wherein the amphiphilic compound is at a concentration, by weight, of about 0.01% to about 0.5%, based upon weight of the composition.

5. The cosmetic composition of claim 1, wherein the surfactant comprises a polysorbate.

6. The cosmetic composition of claim 1, wherein the surfactant is at a concentration, by weight, of about 0.01% to about 0.5%, based upon weight of the composition.

7. The cosmetic composition of claim 1, wherein the aqueous phase comprises water, a preservative, glycerin, and a chelating agent.

8. The cosmetic composition of claim 7, wherein the chelating agent comprises disodium EDTA, tetradsodium EDTA, or combinations thereof.

9. The cosmetic composition of claim 1, wherein the active ingredient is capryloyl salicylic acid.

10. The cosmetic composition of claim 1, wherein the emollient comprises hydrogenated polyisobutene and isohexadecane.

11. The cosmetic composition of claim 1, further comprising a thickening phase.

12. The cosmetic composition of claim 11 wherein the thickening phase comprises dimethicone, sodium polyacrylate, or combinations thereof.

13. The cosmetic composition of claim 1, wherein the viscosity is about 40 Pa·s to about 120 Pa·s measured at a temperature of about 20° C. to about 25° C.

14. The cosmetic composition of claim 1, further comprising a mattifier.

15. The cosmetic composition of claim 14, wherein the mattifier comprises acrylate copolymer, Nylon-12, polyamides, or combinations thereof.

16. A method for treating keratinous tissue comprising applying to the keratinous tissue the composition of claim 1.

17. A process for preparing oil-in-water emulsion cosmetic composition according to claim 1, comprising:
   homogenizing at a predetermined temperature the oil phase;
   adding the oil stabilizing component to the oil phase; and
   mixing the aqueous phase with the oil phase to form the oil-in-water emulsion.

* * * * *